United States Patent [19]

Kern

[11] Patent Number: 5,058,595

[45] Date of Patent: Oct. 22, 1991

[54] JUDKINS-TYPE ANGIOGRAPHIC CATHETER WITH DOPPLER CRYSTAL, AND METHOD OF USE

[75] Inventor: Morton J. Kern, St. Louis, Mo.

[73] Assignee: St. Louis University, St. Louis, Mo.

[21] Appl. No.: 472,767

[22] Filed: Jan. 31, 1990

[51] Int. Cl.$^5$ .............................................. A61B 8/12
[52] U.S. Cl. ................................. 128/662.06; 604/281
[58] Field of Search ........................ 128/662.06, 372; 604/281

[56] References Cited

U.S. PATENT DOCUMENTS

| 4,889,128 | 12/1989 | Millar | 128/662.06 |
| 4,957,111 | 9/1990 | Millar | 128/662.06 |

OTHER PUBLICATIONS

Sibley et al., "Subselective Measurement of Coronary Blood Flow Velocity Using a Steerable Doppler Catheter," Journal of American College of Cardiology, vol. 8, No. 6, Dec. 1986.
Wilson et al., "Measurement of Maximal Coronary Flow Reserve: A Technique for Assessing the Physiologic Significance of Coronary Arterial Lesions in Humans," Herz, 1987.
Hangiandreou et al., "Investigation of the Performance of Two Types of the Doppler Catheter in Vitro," Catheterization and Cardiovascular Diagnosis, 18:108-117 (1989).
King et al,, Coronary Arteriography and Angioplasty.
Wilson et al., "Diagnostic Methods–Coronary Flow Reserve," Circulation, vol. 73, No. 3, Mar. 1986.
Marcus et al., "Measurements of Coronary Velocity and Reactive Hyperemia in the Coronary Circulation of Humans," Circulation Research, vol. 49, No. 4, Oct. 1981.
Hartley et al., "Ultrasonic Sensors for Measuring Coronary Blood Flow," SPIE, vol. 904, Microsensors and Catheter-Based Imaging Technology (1988).

Primary Examiner—Francis Jaworski
Attorney, Agent, or Firm—Senniger, Powers, Leavitt & Roedel

[57] ABSTRACT

A Judkins-type angiographic catheter adapted to be inserted in a coronary artery for measuring the velocity of coronary blood flow, comprising a tube of flexible relatively soft material having a proximal end and a distal end terminating in a tip, a Doppler crystal at the tip of the tube, and a conductor connected to the Doppler crystal and extending lengthwise of the tube. A connector at the proximal end of the catheter connects the conductor to a source of energy to cause the Doppler crystal to emit pulses at predetermined frequency for measuring the velocity of coronary blood flow. The Doppler crystal is relatively small compared to the diameter of said tube and is so located relative to the tube that the crystal is adapted to assume a position generally at the diametrical center of the coronary artery when the tip of the catheter is inserted therein.

6 Claims, 6 Drawing Sheets

JUDKINS-TYPE ANGIOGRAPHIC CATHETER WITH DOPPLER CRYSTAL, AND METHOD OF USE

BACKGROUND OF THE INVENTION

This invention relates generally to medical catheters and, more particularly, to a Judkins-type angiographic catheter which is equipped to measure coronary blood flow velocity, and a method of using such a catheter.

Judkins-type catheters are commonly used by cardiologists to make diagnostic angiograms of the heart and surrounding arteries. However, this type of catheter is not capable of measuring the velocity of coronary blood flow. For this type of measurement, intracoronary angiographic catheters with Doppler crystals have heretofore been used. One such catheter in common use, sometimes referred to as a 2.5 F intracoronary catheter, consists of an inner tube having a Doppler crystal at its distal end or tip, and an outer guide tube surrounding the inner tube to form an annular space between the two tubes through which X-ray contrast media may be delivered to the heart for the purpose of angiographic diagnosis. In use, the catheter is advanced along a guidewire previously inserted into a coronary artery, until the catheter assumes a position wherein the Doppler crystal at the tip of the inner tube is precisely located relative to the artery. While the use of the guidewire insures precise positioning of the crystal for proper measurement of blood flow velocity, manipulation of the guidewire inside the artery requires a high degree of skill and involves some risk of damaging the walls of the artery. Moreover, angiograms taken using this type of catheter are often less than satisfactory due to unfavorable concentrations of X-ray contrast media delivered through the annular space between the two tubes.

Another type of intravascular catheter used to measure coronary blood flow velocity is sometimes referred to as a Sones-Doppler catheter, which is a relatively straight stiff catheter with an annular Doppler crystal at its tip. Sones-type catheters are illustrated on page 142 of *Coronary Arteriography and Angioplasty*, by Spencer King, M.D., incorporated herein by reference. However, Sones-type catheters are difficult to manipulate, and require a high degree of specialized training to use. For example, to place a Sones-type catheter in the left coronary artery requires careful manipulation of the catheter; the catheter is actually manipulated by impinging it against the coronary cusp. This is illustrated on pages 151 and 153 of *Coronary Arteriography and Angioplasty*. Moreover, the stiffness of the catheter, and the hard sharp tip formed by the Doppler crystal, present a risk of internal injuries.

Because of the risks associated with these prior catheterization procedures for measuring the velocity of coronary blood flow, these procedures are not generally justified for patients without coronary artery disease. In contrast with these prior Doppler-equipped catheter, Judkins-type diagnostic catheters are much easier to manipulate, and they present less risk of injury to the patient. The use of these catheters, for example the Judkins-type catheters is relatively safer and more familiar to most cardiologists. However, none of these diagnostic catheters is equipped to measure blood flow velocities in coronary arteries.

SUMMARY OF THE INVENTION

Among the several objects of this invention may be noted the provision of a Judkins-type angiographic catheter which is specially equipped for measuring coronary blood flow velocity; the provision of such a catheter which can be used by most cardiologists without additional specialized training: the provision of such a catheter which is adapted to measure coronary blood flow velocity at accuracies equal to prior intracoronary Doppler angiographic catheters; the provision of such a catheter which is stable in use; the provision of such a catheter which facilitates more rapid and safer measurement of coronary flow velocity in patients; the provision of such a catheter that can be safely used to measure coronary flow velocity in patients where deep cardiac catheterization is not justified, for example those without coronary artery disease; and the provision of a method of using such a catheter.

In general, the catheter of the present invention is a Judkins-type angiographic catheter that is adapted to be inserted in a coronary artery for measuring the velocity of coronary blood flow. The catheter comprises a tube of flexible, relatively soft material having a proximal end and a distal end terminating in a tip. As is well known, in Judkins-type catheters the distal end portion of the tube is preformed into a bent configuration. The distal end portion is flexibly resilient to enable the distal end portion to straighten during insertion of the catheter into a patient's artery but to spring back to its preformed bent configuration once inside the aorta to permit the tip of the tube to be inserted to a position inside the patient's coronary artery. A first lumen extends lengthwise of the tube for the passage of an X-ray contrast media. A Doppler crystal is positioned at the tip of the tube, and conductor means, connected to the Doppler crystal, extends lengthwise of the tube. There is a connector means adjacent the proximal end of the catheter for connecting said conductor means to a source of energy to cause the Doppler crystal to emit pulses at predetermined frequency for measuring the velocity of coronary blood flow.

The Doppler crystal is preferably relatively small compared to the diameter of said tube, and is so located relative to the tube so that the crystal is adapted to assume a position generally at the diametrical center of the coronary artery when the tip of the catheter is inserted therein. The Doppler crystal may either be embedded in the tube wall, or adhesively attached to the tube. The tube may comprise a second lumen, also extending lengthwise of the tube, for carrying said conductor means.

Generally, the method of measuring the velocity of coronary blood flow of this invention comprises the steps of providing a Judkins-type angiographic catheter, comprising a tube of flexible resilient material having a proximal end, a distal end terminating in a tip, a first lumen in the tube extending lengthwise of the tube for passage of an X-ray contrast media therethrough, a Doppler crystal at the tip of the tube, conductor means connected to the Doppler crystal extending lengthwise of the tube, and means adjacent the proximal end of the catheter for connecting said conductor means to a source of energy. A guidewire is inserted through an artery of a patient to a location inside the aorta of the patient. The tube is advanced, tip first, along the guidewire with the guidewire inside said first lumen until the distal end portion of the tube is inside the aorta. The guidewire is removed from the tube while leaving the distal end portion of the tube inside the aorta. The distal end portion of the tube is manipulated to a position wherein the tip of the tube and Doppler crystal are inside the left main coronary artery with the crystal generally at the diametrical center of the coronary artery. The Doppler crystal is energized to cause it to emit pulses at a predetermined frequency for measuring the velocity of coronary blood flow.

The Doppler crystal-equipped Judkins-type catheter of this invention is thus specially adapted for measuring coronary blood flow velocity. Because it is the familiar Judkins-type catheter that is widely used in diagnostic procedures, it can be used by most cardiologists without additional specialized training. Moreover, because it is a Judkins-type catheter, as opposed to an intracoronary catheter or a Sones-type catheter, it allows more rapid and relatively safer velocity measurement. The Judkins-type catheter can even be used to measure blood flow rate in patients without coronary artery disease; heretofore, it was not feasible to measure blood flow rate in these patients because their condition was not sufficiently serious to justify the risks associated with the prior Doppler-crystal equipped intracoronary devices. The Judkins-type catheter measures coronary blood flow velocities with accuracies comparable to prior intracoronary Doppler angiographic catheters.

BRIEF DESCRIPTION OF THE DRAWINGS

Corresponding reference numerals indicate corresponding parts throughout the several views of the drawings.

DETAILED DESCRIPTION OF THE PREFERRED EMBODIMENT

Figures 1, 2, 3:
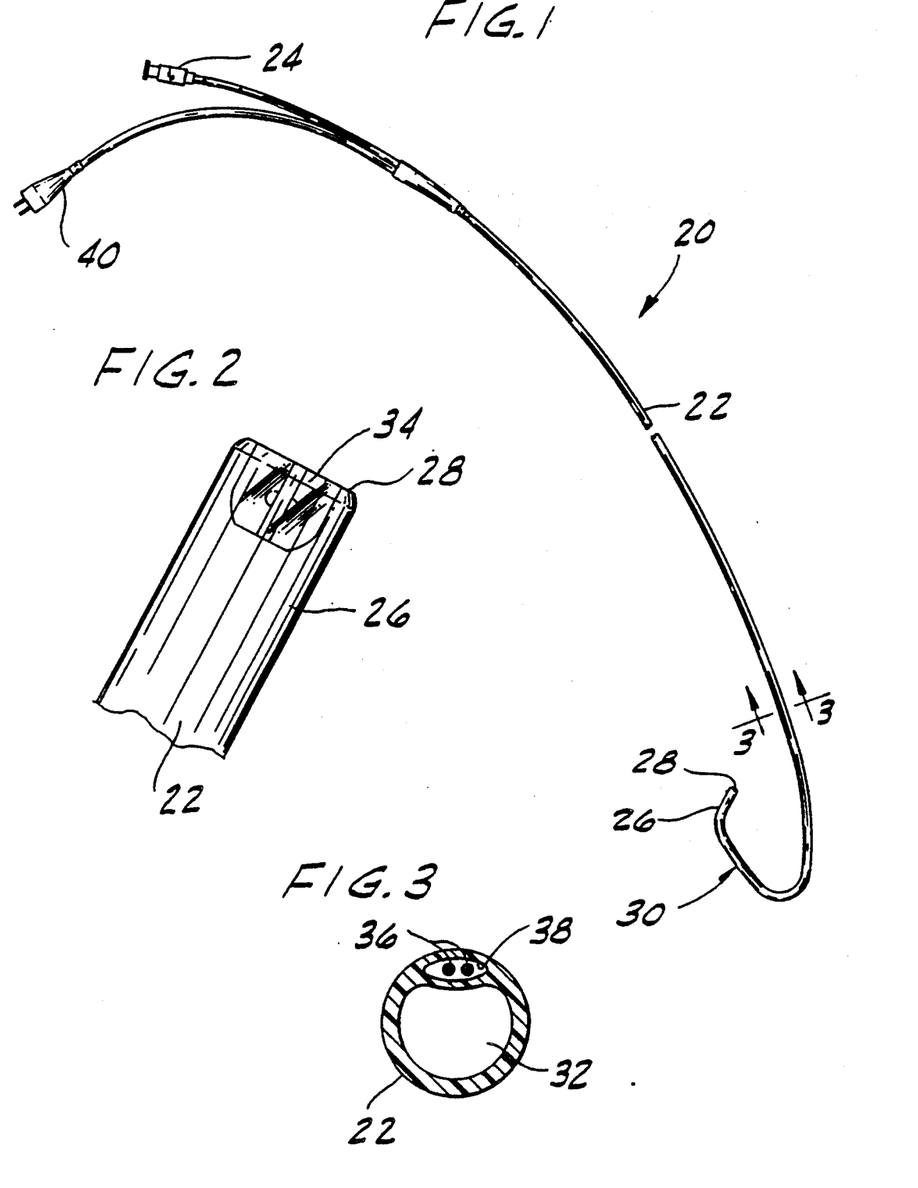
FIG. 1 is a side elevation view of a Judkins-type catheter for measuring coronary flow velocity constructed according to the principles of this invention.
FIG. 2 is an enlarged view of the tip of the catheter of FIG. 1.
FIG. 3 is an enlarged transverse cross-sectional view of the catheter taken along the plane of line 3—3 in FIG. 1.

A Judkins-type catheter constructed according to the principles of this invention is indicated generally as 20 in FIG. 1. The catheter 20 is a basically a standard Judkins-type angiographic catheter, but has been specially adapted for measuring the velocity of blood flow in the left coronary artery. As is well-known in this art, the catheter 20 comprises a tube 22 that is a 8F double lumen extrusion of a flexible, relatively soft material such as polyvinyl chloride catheter material. The tube 22 has a proximal end 24, and a distal end 26 terminating in a tip 28. The distal end portion 30 of the tube is preformed into the standard Judkins L4 bent configuration that is specially adapted for manipulating the tip 28 into the ostium of the left coronary artery. An example of the appropriate configuration of the distal end portion of the catheter is shown on page 186 of *Coronary Arteriography and Angioplasty*. The catheter 10 thus has identical shape and handling characteristics to a left Judkins diagnostic catheter.

The catheter 20 is adapted to be advanced to the patient's ascending aorta over a 0.038" J-tipped safety guidewire using standard diagnostic technique. The distal end portion 30 is flexibly resilient to enable the distal end portion to straighten during insertion of the catheter into a patient's artery over the guidewire, yet spring back to its preformed bent configuration once inside the aorta to permit the tip 28 of the tube to be manipulated into the patient's left coronary artery. The manipulation of the catheter 20 into the coronary artery is shown and described on pages 186–187 of *Coronary Arteriography and Angioplasty*.

A first lumen 32 extends lengthwise of the tube 24 for the passage of an X-ray contrast media. A Doppler crystal 34 is positioned at the tip 28 of the tube. The Doppler crystal is preferably a 20 mHz piezoelectric crystal and is preferably relatively small compared to the diameter of the tube 22. The Doppler crystal is oriented to be in the caudal or "six-o'clock" position relative to the cranial/caudal axis of the patient's left coronary artery, so that when the tip 28 is in the left coronary artery, the crystal 34 is generally at the diametrical center of the coronary artery. This permits the truest reading of the arterial velocity. The crystal 34 may be embedded into the wall of the tube 22, or it may be adhesively secured thereto.

Conductor means, such as lead wires 36, are connected to the Doppler crystal 34, and extend lengthwise of the tube. The wires 36 are located in a second lumen 38, extending length wise of the tube generally parallel to the first lumen but of much smaller diameter. See FIG. 3. Alternatively, the wires 36 may be embedded in the wall of the tube. A connector 40 is at the proximal end of the wires 36, adjacent the proximal end of the catheter, for connecting the wires to a velocity measuring device including a source of energy to cause the Doppler crystal to emit ultrasonic pulses at predetermined frequency, and means for receiving signals generated by the reflected ultrasonic pulses for measuring the velocity of blood flow through the left coronary artery.

The method of measuring the velocity of coronary blood flow of this invention comprises the steps of providing a Judkin's-type angiographic catheter 20, as described above. The catheter 20 comprises a flexible tube 22 having a proximal end 24 and a distal end 26 terminating in a tip 28. The catheter 20 also comprises a first lumen 32 in the tube extending lengthwise of the tube for passage of an X-ray contrast media therethrough. A Doppler crystal 34 is located at the tip 28 of the tube, and connected by wires 36 to connector 40.

Figure 4:
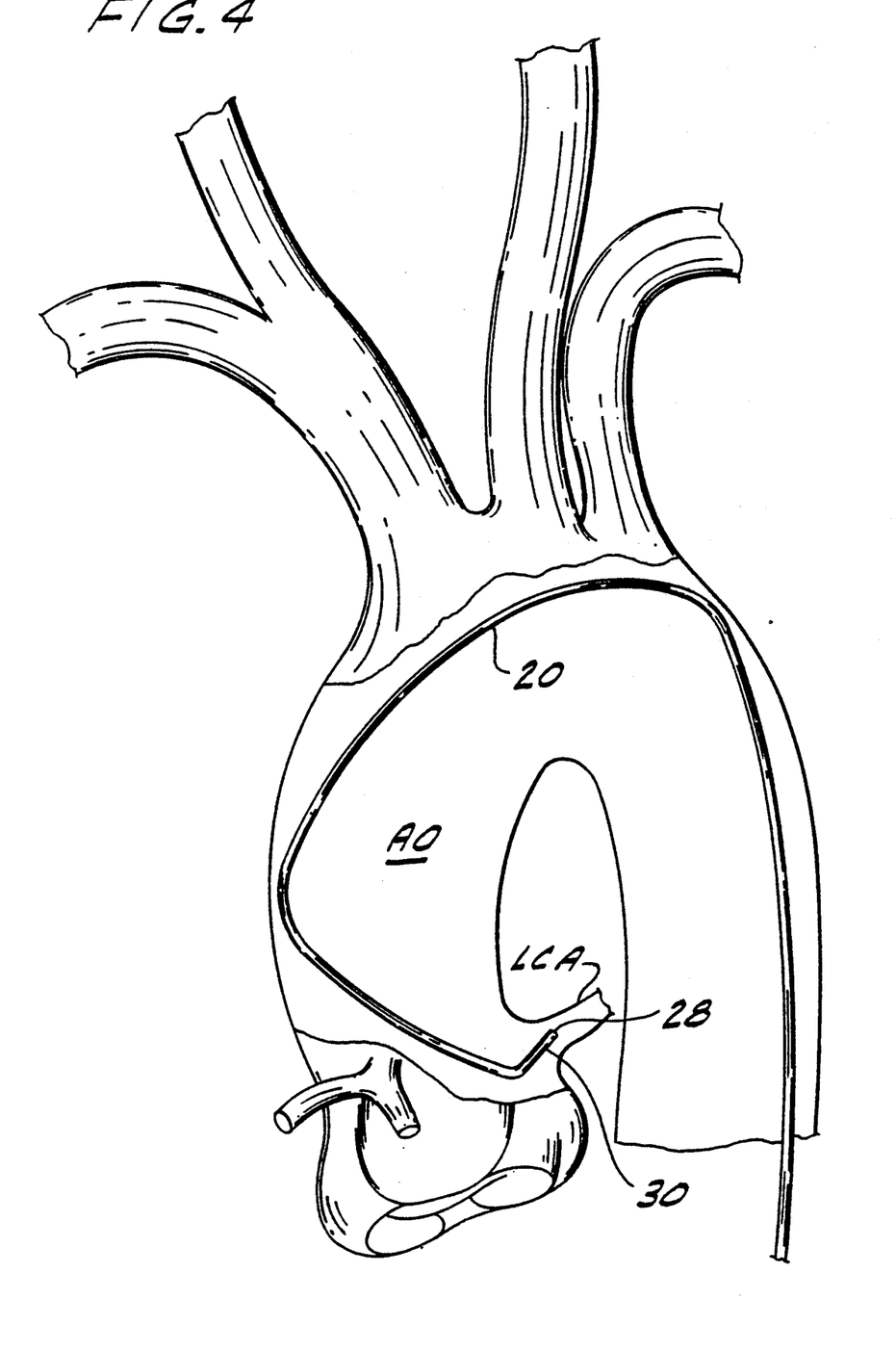
FIG. 4 is a side elevation view of the aorta showing the placement of the distal end of the catheter of FIG. 1 in the left coronary artery.

The catheter 20 is placed by first inserting a 0.038" J-tipped safety guidewire through an artery of the patient to a location in the aorta of the patient. The catheter is advanced, tip first, along the guidewire (with the guidewire inside said first lumen) until the distal end portion of the tube is inside the aorta. The guidewire is removed from the tube while leaving the distal end portion of the tube inside the aorta (AO in FIG. 4). The distal end portion 30 of the tube is manipulated to a position shown in FIG. 4 wherein the tip 28 of the tube and Doppler crystal 34 are inside the left main coronary artery (LCA) with the crystal generally at the diametrical center of the coronary artery.

Once the catheter 20 is properly placed the Doppler crystal is energized to cause it to emit pulses of ultrasound at predetermined frequencies. The Doppler crystal also acts as a receiver of the pulses reflected back, chiefly by red blood cells flowing in the coronary artery. The reflected signals are "gated" to control the range from which the reflections are received (typically 2–4 mm). The shift in the frequency of the reflected ultrasound (according to the Doppler principle) can be used to determine the velocity of the flow in the coronary artery. The use of ultrasonic sensors for measuring coronary blood flow is explained in Hartley and Millar, "Ultrasonic Sensors for Measuring Coronary Blood Flow", SPIE Vol. 904, *Microsensors and Catheter-Based Imaging Technology* pp/ 17–22 (1988), incorporated herein by reference.

Once the flow velocity through the left coronary artery is measured, the coronary flow velocity reserve can be determined by measuring the flow velocity during hyperemia, such as might be induced by the administration of papaverine.

OPERATION

The operation of the Judkins-type catheter 20 of this invention was verified as follows:

TEST 1

In vivo studies in 6 dogs were conducted to test the feasibility of the catheter, and to demonstrate that the Judkins-type catheter did not interfere with intracoronary flow velocity. Simultaneous measurements of coronary velocity were made with the Judkins-type catheter and a surgically implanted cuff-type coronary velocity transducer. The transducer was a hard epoxy coronary cuff Doppler (20 mHz) velocity probe Model HDP-30-2U (from Crystal Biotech, Hollington, Mass.), connected to a VF-1 pulsed Doppler amplifier, Model 1D-1 (from Crystal Biotech, Hollington, Mass.). The Judkins-type catheter was inserted through an 8F valved sheath in the carotid artery and positioned under fluroscopic control in the ostia of the left coronary artery. Simultaneous signals from the Judkins-type and the cuff-type Dopplers were recorded.

Figure 5:
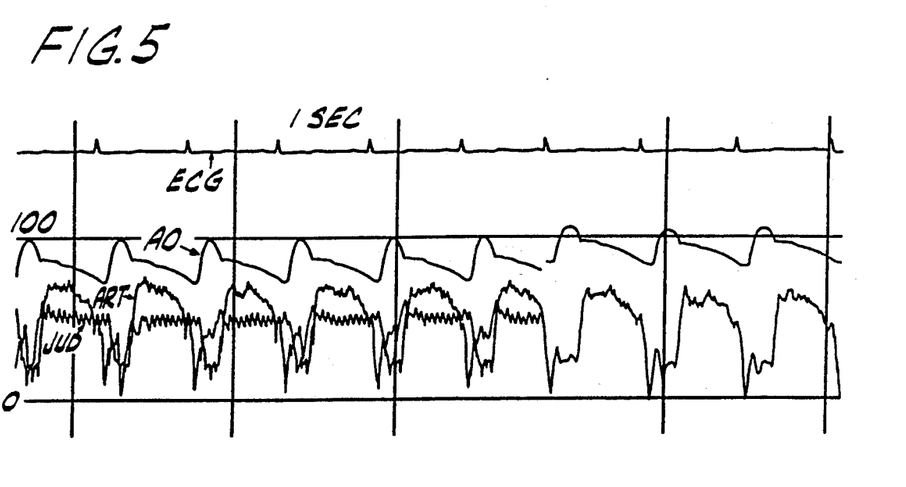
FIG. 5 is a graph of simultaneous Doppler velocity tracings obtained from a Judkins-type catheter of this invention (JUD) and a surgically implanted cuff type velocity transducer (ART) in a dog.

Comparison between the surgically implanted cuff-type Doppler signals and the Judkins-type Doppler signals in the left coronary arteries of dogs confirmed a temporal and configurational similarity of the diastolic flow velocity characteristics. See FIG. 5 where the readings for the Judkins-type catheter are labeled JUD and the readings for the cuff-type transducer are labeled ART. A satisfactory correlation was evidenced for duration of diastolic flow velocity and total diastolic flow velocity integral. Mean and peak phasic velocities were also similar, but because of differences in the amplifiers, the arterial placement, and non-parallel responses between the two systems, the absolute values differed.

TEST 2

Nineteen patients undergoing routine diagnostic catheterization for chest pain were studied. All cardioactive medications were withheld 12–18 hours before the study, and in a fasting state the patients underwent a routine diagnostic catheterization, which revealed angiographically normal coronary arteries and ventricular function. After this diagnostic study, coronary velocity and coronary vasodilatory reserve were measured with both Judkins-type catheters constructed according to the principles of this invention and DC-101 2.5F Doppler velocity catheters (from Millar Instruments, Houston, Tex.). (The protocol for the measurement of coronary vasodilatory reserve was approved by the Human Subjects Research Committee of the St. Louis University Institution Review Board.)

The Judkins-type catheter was positioned in the left coronary ostia using standard diagnostic catheter technique. Coronary flow velocity and arterial pressure before and during hyperemia were measured, and recorded along with electrocardiographic signals (lead II) Intracoronary velocity and arterial pressure were recorded continuously at rest and during hyperemia induced by the administration of papaverine (10 mg in 10 cc normal saline) delivered through the catheter into the left main coronary artery and for 90–120 seconds thereafter. After 3 minutes, a second 10–12 mg dose of papaverine was administered to assess achievement of maximum hyperemia.

The Millar DC-101 2.5F Doppler velocity catheter was inserted over a 0.014" flexible angioplasty guidewire using an 8F guiding catheter. The velocity catheter was positioned in the proximal left main coronary artery. The guiding catheter was flushed and filled with saline, and phasic and mean arterial pressures were measured through the fluid-filled lumen. Intracoronary velocity and arterial pressure were recorded as described above.

The Judkins-type catheter 20 was advanced to the aorta over a 0.038" J-tipped safety guidewire using standard diagnostic techniques, and the tip was positioned in the left coronary ostia. Velocity signal generation and processing was accomplished with a MDV20 Millar instruments velocimeter, that was calibrated and range-gated for use with a 2.5F Model DC101 doppler catheter from Millar Instruments. Satisfactory Doppler velocity signals were obtained in 85% of the patients tested, and these signals were identical in timing, duration, and diastolic wave form to an intracoronary doppler velocity signal at the same location.

Figure 6A:
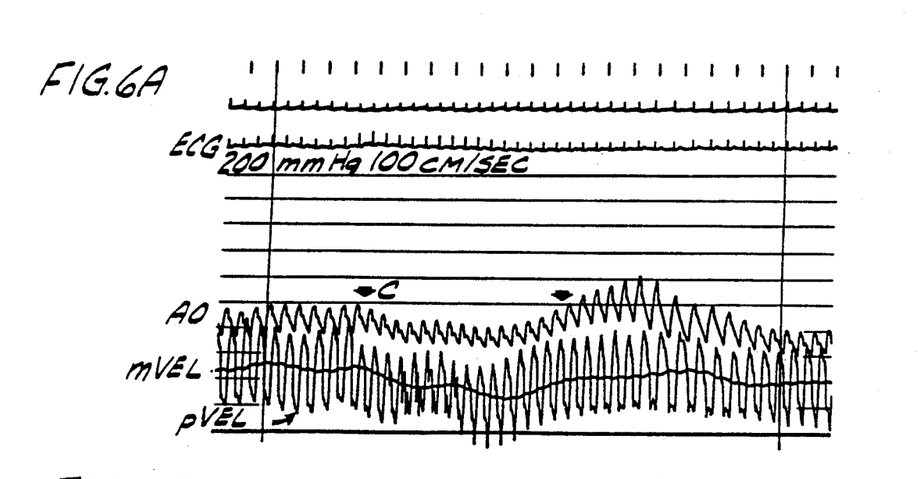
FIG. 6A is a graph illustrating normal sinus arythmia with respiratory variation in aortic pressure.
Figure 6B:
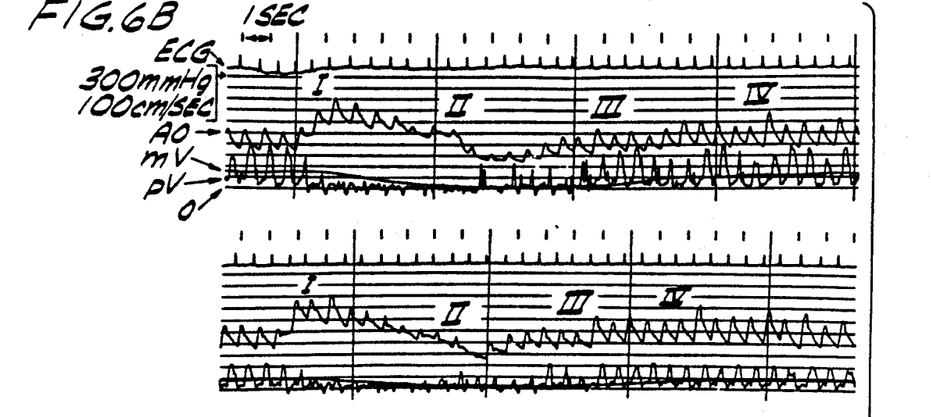
FIG. 6B are two graphs comparing the velocities measured during Valsalva by the Judkins-type catheter of this invention and by a prior art catheter.
Figure 6C:
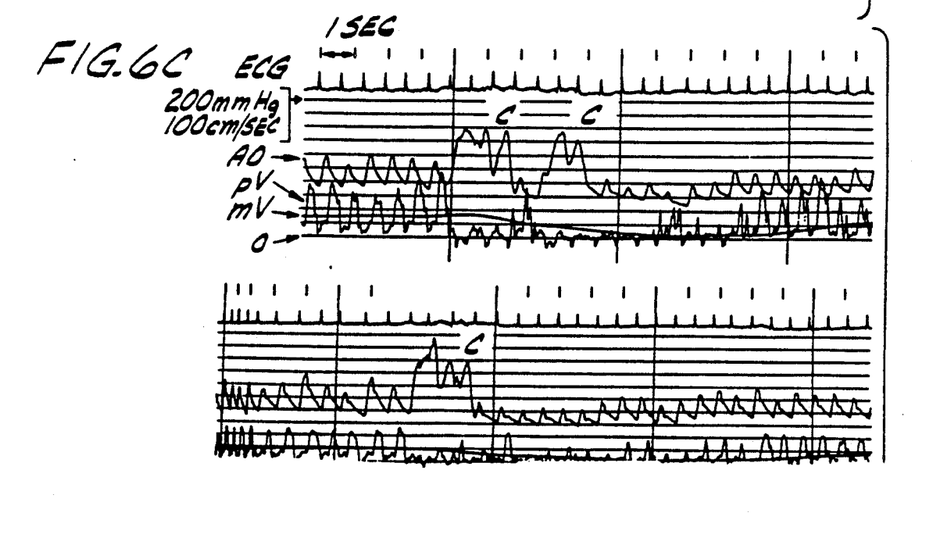
FIG. 6C are two graphs comparing the velocities measured during a cough by the Judkins-type catheter of this invention and by a prior art catheter.

To assess stability with regard to respiration and catheter movement, duplicate recordings during cough and Valsalva were made with both the Judkins-type and DC-101 catheters in six patients. This data is illustrated graphically in FIGS. 6B and 6C. In these Figures ECG denotes electrocardiogram; AO denoted aortic pressure mV denotes mean velocity; and pV denotes phasic velocity. FIG. 6A shows normal sinus arythmia with respiratory variation in aortic pressure demonstrating tracking of mean and phasic ostial coronary velocity (designated mVEL and pVEL, respectively). The arrow marks the inspiratory fall in aortic pressure and corresponding decline in coronary flow velocity. FIG. 6B shows paired velocity trackings during Valsalva measured with the Judkins-type catheter (upper) and the Millar type catheter (lower). FIG. 6C shows the paired velocity trackings during cough measured with the Judkins-type catheter (upper) and the Millar type catheter (lower). The Doppler velocities behave similarly, demonstrating the similarity in response during normal respiration and respiratory maneuvers.

In ten of the patients, the velocity was measured by with the Judkins-type catheter followed by the Millar catheter, in the other nine patients the order of measurement was reversed.

Figure 7:
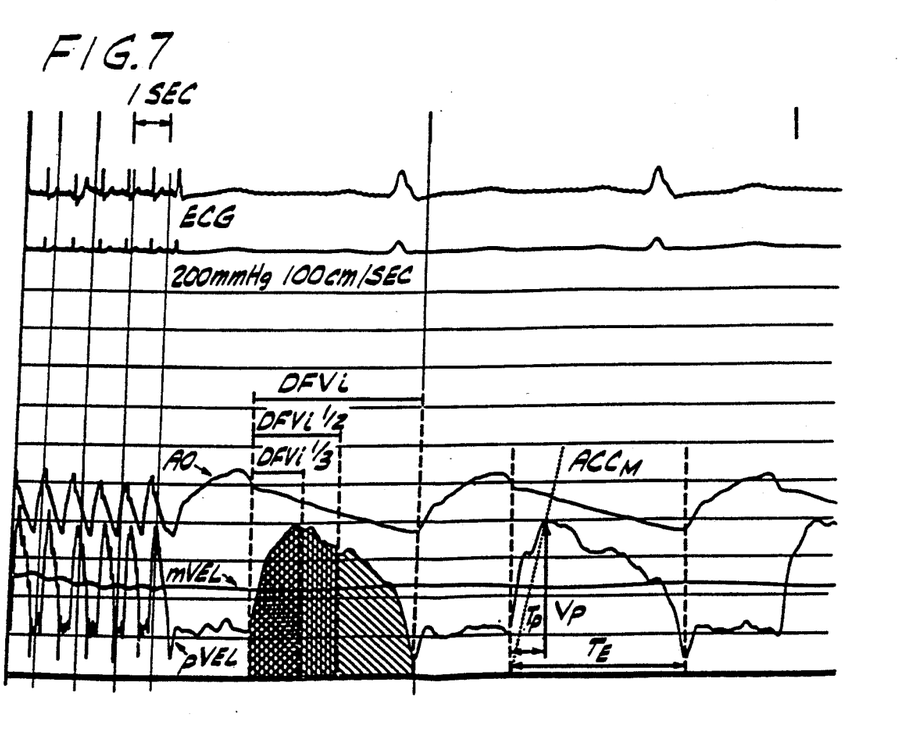
FIG. 7 is a graph illustrating the various parameters measured in the comparison testing of the Judkins-type catheter of this invention.

The Doppler velocity signals were analyzed by computer-assisted digitizing (from Summagraphics, Inc.) of the velocity wave forms with custom designed software. The following variables were analyzed: duration of diastolic flow ($T_t$), diastolic flow velocity integral (DFVi), one-third (DFVi⅓) and one half (DFVi½) of the diastolic flow velocity integral, time to peak velocity ($T_{pk}$), and peak phasic and mean velocities. These parameters are illustrated in FIG. 7. Coronary vasodilatory reserve was computed in two ways: (1) the ratio of peak hyperemic to basal mean flow velocity (CVR), and (2) CVR normalized for pressure.

The results of the test are given in TABLE I. Data were analyzed by one-way analysis of variance and utilized Duncan's multiple range F statistic for multiple comparison of the means. First order linear regression and correlation coefficients (SYSTAT program) were used to compute similarity of in vivo data obtained with the Judkins-style and Millar catheters. In discrete subanalyses, paired or unpaired t tests were utilized where appropriate with probability (p) values considered significant when $p < 0.05$. Results are expressed as mean ±1 standard deviation unless otherwise indicated. It is clear from TABLE I that there were no significant differences in the coronary vasodilatory reserve (CVR and CVR Norm) calculated by either technique. Although the coronary vasodilatory reserve calculated in the same patient at approximately the same coronary location was nearly the same for both techniques, the magnitude of the mean (M Vel) and peak phasic (P Vel) velocity signals was greater for the Judkins-type than the Millar catheter. These differences may be due to slightly deeper position, differences in Doppler angle, or range gate within the same artery. Velocity variations may also occur due to changes in artery diameter or flow disturbances due to the take-off point of large side branches, but are most likely related to sampling position and volume which cannot be precisely duplicated by the two techniques.

TABLE I

| | (TEST 2) | | | |
|---|---|---|---|---|
| | Judkins | | 2.5 Doppler | |
| n = 19 | Rest | Papaverine | Rest | Papaverine |
| SYS | 137 ± 28 | 124 ± 25 | 139 ± 29 | 124 ± 24 |
| DIA | 79 ± 11 | 72 ± 9 | 81 ± 13 | 75 ± 11 |

TABLE I-continued

| | (TEST 2) | | | |
|---|---|---|---|---|
| | Judkins | | 2.5 Doppler | |
| n = 19 | Rest | Papaverine | Rest | Papaverine |
| MAP | 98 ± 16 | 89 ± 13 | 101 ± 16 | 91 ± 14 |
| HR | 73 ± 16 | 77 ± 15 | 74 ± 16 | 78 ± 16 |
| DFVi | 6.9 ± 4.1 | 20.8 ± 11.0 | 4.7 ± 3.0 | 15.7 ± 8.2 |
| DFVi/3 | 35 ± 10 | 35 ± 8 | 38 ± 10 | 36 ± 11 |
| DFVi/2 | 59 ± 11 | 56 ± 9 | 56 ± 8 | 56 ± 10 |
| Tt | 0.52 ± 0.12 | 0.51 ± 0.10 | 0.52 ± 0.14 | 0.50 ± 0.13 |
| Tpk | 0.16 ± 0.05 | 0.18 ± 0.06 | 0.15 ± 0.06 | 0.18 ± 0.07 |
| M Vel | 13.7 ± 7.9 | 40.5 ± 18.2 | 9.6 ± 6.5 | 31.7 ± 14.2 |
| P Vel | 21.8 ± 10.5 | 58.0 ± 21.0 | 14.9 ± 8.5 | 47.7 ± 16.9 |
| CVR | — | 3.33 ± 1.36 | — | 3.72 ± 1.20 |
| CVR Norm | — | 0.35 ± 0.15 | — | 0.29 ± 0.15 |

Table 1 also indicates that there were no significant differences in the total time of diastolic flow ($T_t$), the time to peak ($T_{pk}$), the first one-third (DFVi⅓) and the first one-half (DFVi½) distolic flow velocity integrals.

Figure 8A:
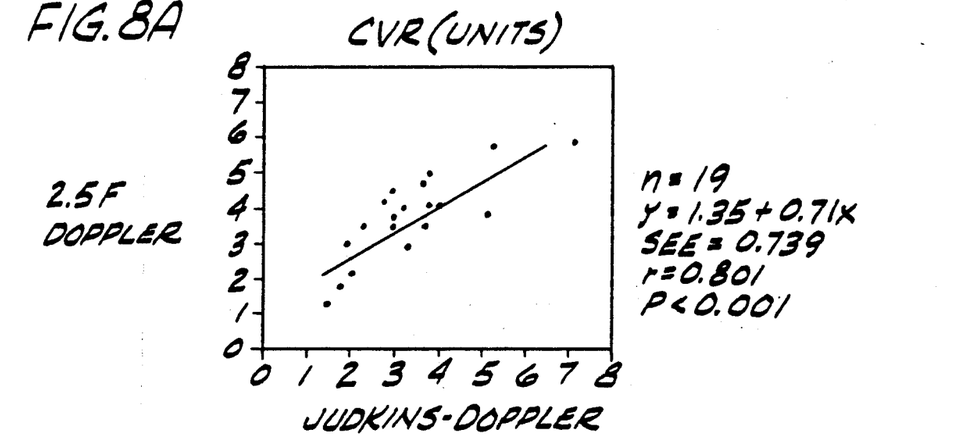
FIG. 8A is a graph showing the correlation between the coronary vasodilatory reserve measured by the Judkins-type catheter of this invention and by a prior art catheter.
Figure 8B:
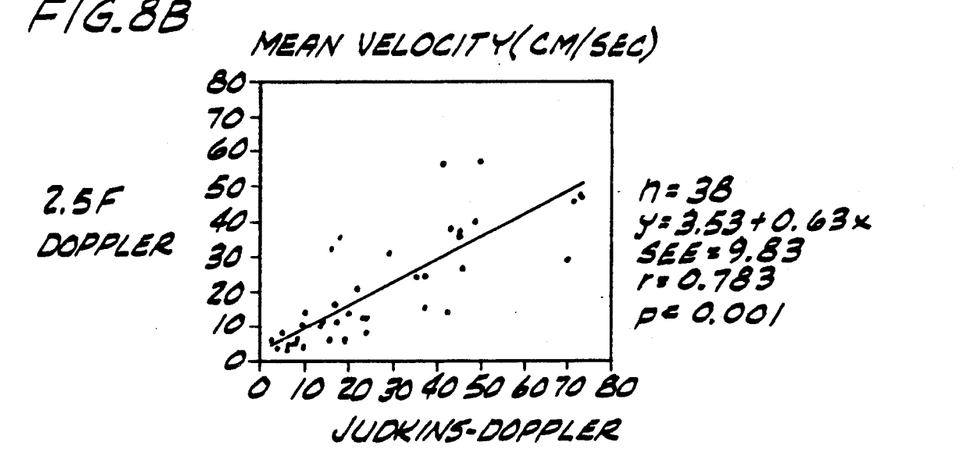
FIG. 8B is a graph showing the correlation between the mean velocity measured by the Judkins-type catheter of this invention and by a prior art catheter.
Figure 8C:
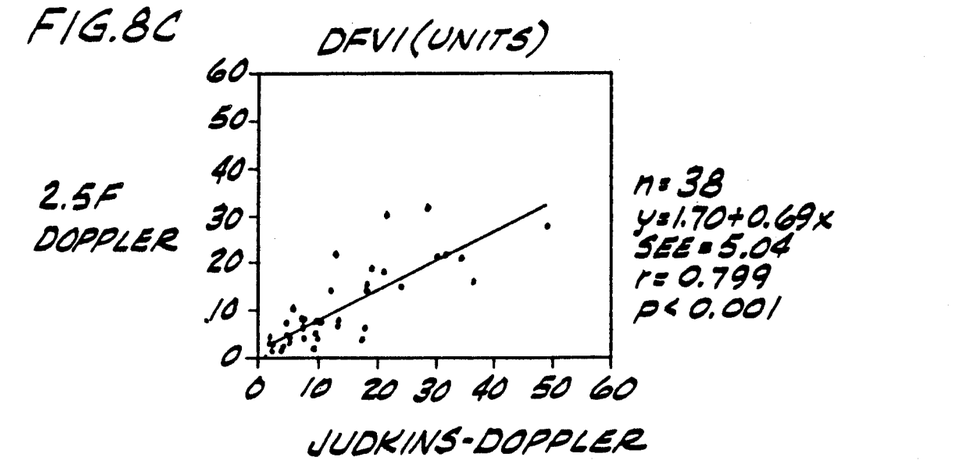
FIG. 8C is a graph showing the correlation between the diastolic flow velocity integral measured by the Judkins-type catheter of this invention and by a prior art catheter.
Figure 9:
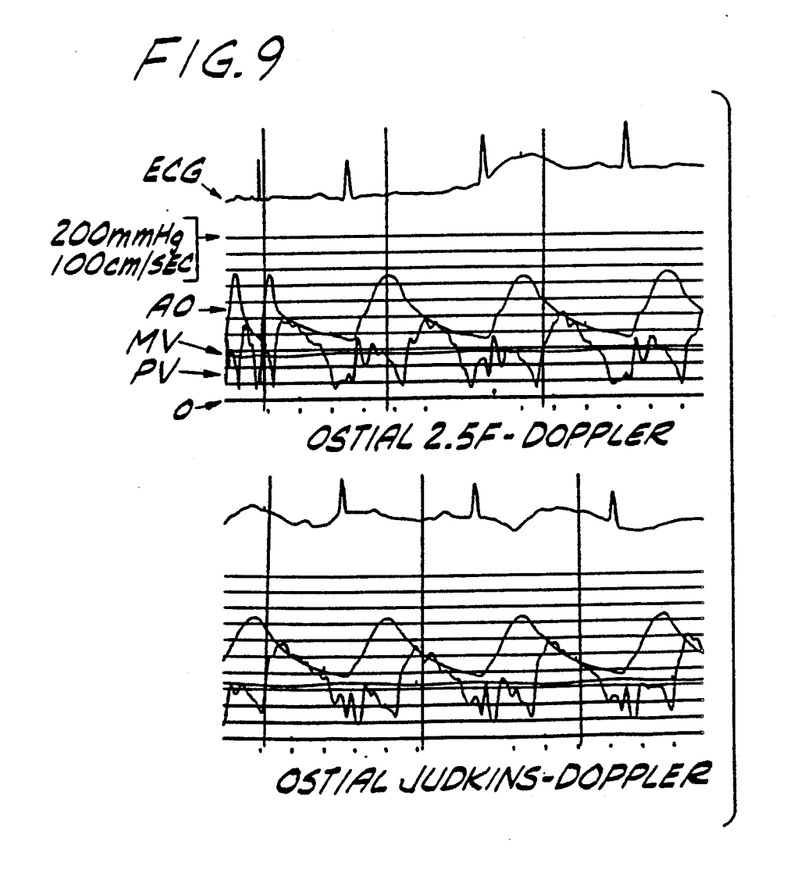
FIG. 9 is a graph comparing the velocities measured by the Judkins-type catheter of this invention and by a prior art catheter.

FIGS. 8A, 8B and 8C compare the coronary vasodilatory reserve mean velocity and the diastolic flow velocity integral. FIG. 9 are graphs comparing the Mean Velocity and Peak Velocity for the Millar (upper) and Judkins-type (lower) catheters for the same patient, showing similarity in wave form between the two.

It will be apparent from the foregoing that the Judkins-type catheter of this invention, and the method of using the Judkins-type catheter, accurately measure arterial blood flow velocity.

In view of the above, it will be seen that the several objects of the invention are achieved and other advantageous results attained As various changes could be made in the above constructions without departing from the scope of the invention, it is intended that all matter contained in the above description or shown in the accompanying drawings shall be interpreted as illustrative and not in a limiting sense.

What is claimed is:

1. A Judkins-type angiographic catheter adapted to be inserted in a coronary artery for measuring the velocity of coronary blood flow, comprising a tube of flexible relatively soft material having a proximal end and a distal end terminating in a tip, a first lumen in the tube extending lengthwise of the tube for passage of an X-ray contrast media therethrough, a Doppler crystal affixed to the tube at the tip of the tube, conductor means connected to the Doppler crystal extending lengthwise of the tube, and means adjacent the proximal end of the catheter for connecting said conductor means to a source of energy to cause the Doppler crystal to emit pulses at predetermined frequency for measuring the velocity of coronary blood flow, said tube having a distal end portion preformed into a bent configuration, said distal end portion being flexibly resilient for enabling the distal end portion to straighten during insertion of the catheter into the body and to spring back to its preformed bent configuration once inside the heart to permit the tip of the tube to be inserted to a position inside a patient's coronary artery.

2. A catheter as set forth in claim 1 wherein said Doppler crystal is relatively small compared to the diameter of said tube and is so located relative to the tube that the crystal is adapted to assume a position generally at the diametrical center of the coronary artery when the tip of the catheter is inserted therein.

3. A catheter as set forth in claim 2 wherein said tube has a annular wall and said Doppler crystal is embedded in the wall.

4. A catheter as set forth in claim 2 wherein said Doppler crystal is adhesively attached to the tube.

5. A catheter as set forth in claim 1 further comprising means defining a second lumen within said tube extending lengthwise of the tube for carrying said conductor means.

6. A method of measuring the velocity of coronary blood flow using a Judkin's type angiographic catheter, said method comprising the steps of
   providing a tube of flexible resilient material having a proximal end and a distal end terminating in a tip, a first lumen in the tube extending lengthwise of the tube for passage of an X-ray contrast media therethrough, a Doppler crystal affixed to the tube at the tip of the tube, conductor means connected to the Doppler crystal extending lengthwise of the tube, and means adjacent the proximal end of the catheter for connecting said conductor means to a source of energy, said tube having a distal end portion preformed into a bent configuration, inserting a guidewire through an artery of a patient to a location inside the aorta of the patient,
   advancing the tube, tip first, along the guidewire with the guidewire inside said first lumen until the distal end portion of the tube is inside the aorta, said distal end portion of the tube being adapted to straighten as it is advanced along the guidewire,
   removing the guidewire from the tube while leaving the distal end portion of the tube inside the aorta, said distal end portion being adapted to spring back to its said preformed bent configuration when the guidewire is removed,
   manipulating the preformed bent distal end portion of the tube to a position wherein the tip of the tube and Doppler crystal are inside the left main coronary artery with the crystal generally at the diametrical center of the coronary artery, and
   energizing said Doppler crystal to cause it to emit pulses at predetermined frequency for measuring the velocity of coronary blood flow.

* * * * *